(12) United States Patent
Boezaart

(10) Patent No.: US 9,168,351 B2
(45) Date of Patent: Oct. 27, 2015

(54) INSTRUMENT FOR CONTINUOUS DISCHARGE OF ANESTHETIC DRUG

(76) Inventor: Andre P. Boezaart, Gainesville, FL (US)

( * ) Notice: Subject to any disclaimer, the term of this patent is extended or adjusted under 35 U.S.C. 154(b) by 1164 days.

(21) Appl. No.: 12/547,708

(22) Filed: Aug. 26, 2009

(65) Prior Publication Data

US 2011/0054383 A1   Mar. 3, 2011

(51) Int. Cl.
*A61M 19/00* (2006.01)
*A61N 1/05* (2006.01)

(52) U.S. Cl.
CPC ............... *A61M 19/00* (2013.01); *A61N 1/0551* (2013.01)

(58) Field of Classification Search
CPC ........... A61B 17/3401; A61B 18/1492; A61N 1/0551; A61M 2025/0007; A61M 19/00
USPC .......... 604/20, 21, 158, 510, 512, 912; 607/7; 600/470
See application file for complete search history.

(56) References Cited

U.S. PATENT DOCUMENTS

| 5,024,655 A | * | 6/1991 | Freeman et al. | 604/509 |
| 2008/0195034 A1 | * | 8/2008 | Hafer et al. | 604/21 |
| 2009/0062871 A1 | * | 3/2009 | Chin et al. | 606/86 R |

* cited by examiner

*Primary Examiner* — Imani Hayman
(74) *Attorney, Agent, or Firm* — Timothy J. Bechen; Bechen PLLC

(57) ABSTRACT

The present invention is directed towards instruments and methods for discharging an anesthetic drug on a continuous basis for use as a nerve block. In accordance with the present invention, a catheter assembly is provided that comprises an electrically conductive wire, a protective sheath and an inflatable balloon. The inflatable balloon is at the distal end of the catheter capable of being inflated and deflated. A balloon channel terminates within the inflatable balloon at the distal end of the catheter and extends proximally along the length of the catheter to the proximal end of the catheter. The balloon channel has a balloon channel opening at a distal end of the balloon channel within the inflatable balloon, capable of releasing an injected substance into the inflatable balloon. The balloon channel further has a balloon channel injection opening at a proximal end of the balloon channel, capable of receiving an injected substance.

2 Claims, 3 Drawing Sheets

INSTRUMENT FOR CONTINUOUS DISCHARGE OF ANESTHETIC DRUG

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

Embodiments of the invention described herein generally relate to the discharge of anesthetic drug. More specifically, embodiments of the present invention are directed towards instruments and methods for discharging an anesthetic drug on a continuous basis for use as a nerve block.

BACKGROUND OF THE INVENTION

Regional anesthesia refers to anesthetizing only a region of the body, usually in the region where surgery is performed or where acute or chronic pain from any other cause is present. A nerve block accomplishes this task, by administering a local anesthetic agent, such as novocaine, bupivacaine or lidocaine, to the plexus of a nerve. Traditionally, a nerve block was administered using a needle to locate the target nerve and to then insert the anesthetic agent through the needle in order to make contact with the nerve, commonly referred to as a single injection nerve block or single-shot nerve block. One of the major disadvantages of single injection nerve blocks was that the duration of acute pain would be longer than the duration of the single injection nerve block.

As a result, continuous nerve blocks emerged, which utilized an epidural catheter that was threaded through a needle once the needle was properly placed adjacent to the target nerve, and used to deliver variable amounts of the anesthetic agent to the target nerve. In order to properly position the needle on or near the target nerve, a nerve stimulator, such as an electrical current, would be used. Later advances utilized a nerve stimulator on the epidural catheter as well, in order to properly position the epidural catheter on or near the target nerve.

More recently, continuous nerve blocks have been utilized where a needle is properly placed adjacent to the target nerve using ultrasound technology, instead of a nerve stimulator. Subsequent to the proper placement of the needle, an epidural catheter is threaded through the needle and positioned on or near the nerve using a nerve stimulator. However, the major disadvantage to this existing technique is that the catheter is not reliably visible using ultrasound technology, which in turn prevents the epidural catheter to be optimally positioned on or near the target nerve. For example, the current technique requires that the catheter be advanced far down along the nerve to ensure that it is positioned on the nerve for the duration of the continuous block, which in turn may result in coiling of the catheter around the nerve, potentially causing damage to the nerve upon removal of the catheter. In addition, coiling of the catheter is not visible using ultrasound technology, as such technology only allows for a two dimensional view. Furthermore, the current technique requires tunneling of the catheters in order to avoid any dislodgment of the catheters, which also leads to potential damage to the nerves from broken or leaking catheters, as well as infections.

Therefore, there exists a need for a catheter instrument that is visible on an ultrasound image, which would allow for the catheter to be optimally positioned on or near a target nerve and avoid any potential damage from coiling or tunneling of the catheter.

SUMMARY OF THE INVENTION

The present invention is directed towards instruments and methods for discharging an anesthetic drug on a continuous basis for use as a nerve block. In accordance with the present invention, a catheter is provided that comprises an electrically conductive wire, a protective sheath and an inflatable balloon. The electrically conductive wire has a distal end terminating at an electrically conductive wire tip at a distal end of the catheter. A proximal end of the electrically conductive wire extends proximally beyond a proximal end of the catheter, the electrically conductive wire being capable of conveying an electrical impulse from the proximal end of the wire to the wire tip. The sheath comprises a central bore and an outer surface, the sheath covering the central portion of the catheter and a portion of the wire. The balloon is at the distal end of the catheter capable of being inflated and deflated. A balloon channel terminates within the inflatable balloon at the distal end of the catheter and extends proximally along the length of the catheter to the proximal end of the catheter. The balloon channel, within the inflatable balloon, has a balloon channel opening at a distal end of the balloon channel, capable of releasing an injected substance into the balloon. The balloon channel further includes a channel injection opening at a proximal end of the balloon channel, capable of receiving an injected substance. According to one embodiment, the catheter may be fed through a needle assembly into the body of a patient. According to another embodiment, the catheter may be placed over the length of a needle assembly into the body of a patient.

The proximal end of the electrically conductive wire allows for contact with an electrical impulse, which allows for the electrically conductive wire to be placed adjacent to the target nerve. The balloon channel injection opening can be attached to an apparatus, such as a syringe, which would allow for the injection of a liquid or gaseous substance, such as air or saline, in order to expand the inflatable balloon and properly position the catheter using ultrasound technology. Once the catheter is properly and securely positioned, an anesthetic drug can be administered to the target nerve through the central bore of the catheter, by facilitating the attachment of a device for the delivery of the anesthetic through the proximal end of the catheter.

In another embodiment, a second inflatable balloon located at the central portion of the catheter can be inflated, which would allow for the first inflatable balloon to be deflated, while keeping the catheter securely fastened. The first inflatable balloon could be re-inflated at any time in order for an ultra sound image to confirm that the catheter is securely positioned.

Using the above described apparatuses solves the disadvantage of the existing technique of placing a catheter into a body for continuous administration of an anesthetic, namely allowing for the epidural catheter to be optimally positioned on or near the target nerve through ultrasound technology. By utilizing the above-described inflatable balloon, the distal end of the catheter becomes visible on an ultrasound image, allowing for the distal end of the catheter to be properly positioned on or near the target nerve. In addition, by utilizing the inflatable balloon, the catheter can maintain its correct positioning on or near the nerve, without requiring the catheter be placed far down along the nerve, which in turn avoids any potential damage that may result in coiling of the catheter around the nerve. Furthermore, the inflatable balloon also the necessity of tunneling of the catheter, which in turns helps to prevent any potential damage to the nerve upon removal of the catheter.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE EMBODIMENTS

In the following description, reference is made to the accompanying drawings that form a part hereof, and is shown by way of illustration specific embodiments in which the invention may be practiced. It is to be understood that other embodiments may be utilized and structural changes may be made without departing from the scope of the present invention.

Figure 1:
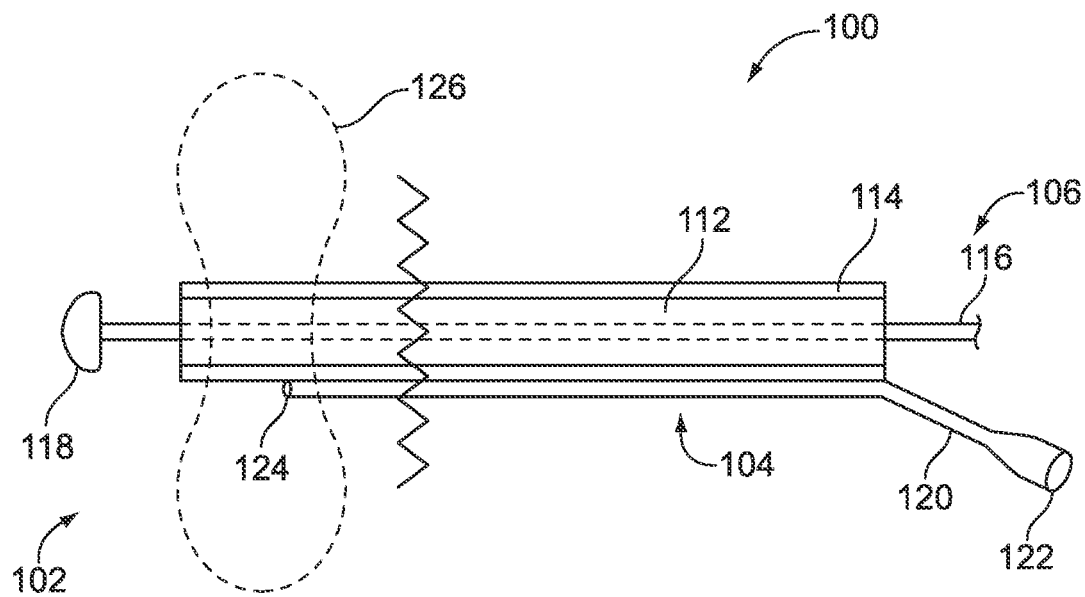
FIG. 1 presents a side elevational view of a catheter assembly.

FIG. 1 presents a side elevational view of a catheter assembly 100. The catheter assembly 100 is of a diameter which allows the assembly to be inserted through a typical needle assembly and into the body of the patient. According to one embodiment, the catheter assembly has a diameter range of twelve (12) to twenty-two (22) gauge. The catheter assembly 100 includes three portions: a central portion 104, a proximal portion 106 and a distal portion 102. The catheter assembly 100 is placed in the body of the patient with the distal portion 102 entering the body first.

Figure 2A:
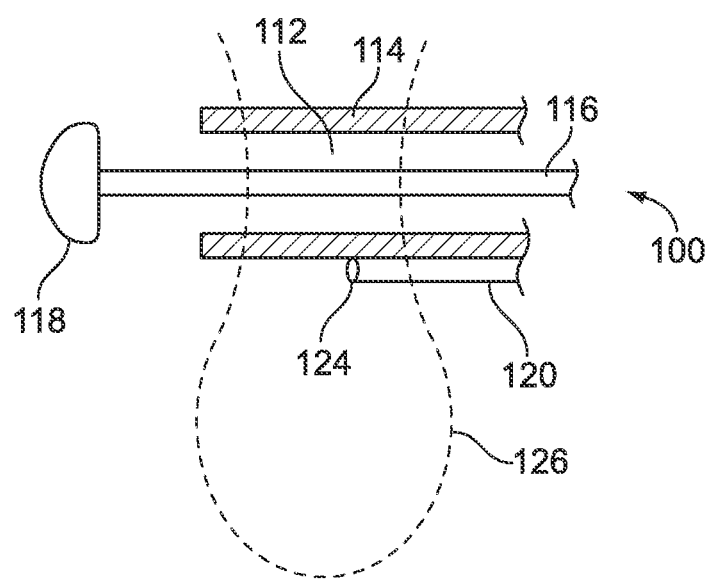
FIG. 2a presents a side elevational view of a portion of the catheter assembly between the distal and proximal ends.

The catheter assembly 100 includes an electrically conductive wire 116, best shown in FIG. 2a, which spans the length of the catheter assembly 100. At the central portion 104 of the catheter assembly 100, a sheath 114 covers the electrically conductive wire 116. The sheath 114 is formed from a thermoplastic or some other similar material in order to insulate an electrical charge that will be conducted through the wire 116. The sheath 114 defines a central bore 112 through which a liquid may pass freely. At the proximal portion 106 of the catheter assembly 100, the wire 116 is not covered by the sheath 114 and has a length that is shorter relative to central portion 104 of the catheter assembly 100. The wire 116 is left exposed so that an electrical charge can make contact with it, in order to conduct an electrical charge down its entire length. According to one embodiment, an electric stimulator as is known in the art, can make contact with the exposed portion of the wire 116 in order to provide the electrical charge.

The distal portion 102 of the catheter assembly 100 also has a length that is shorter relative to central portion 104 of the catheter assembly 100 and is not covered by the sheath 114. The electrically conductive wire 116 is left exposed at the distal portion 102 in order to allow the electrical charge to make contact with a target nerve (Not shown). Attached to the electrically conductive wire 116 at the distal portion 102 is an electrically conductive tip 118, which in one embodiment, is a rounded tip made of a material capable of conducting an electrical current. According to one embodiment, the electrically conductive tip 118 is a piece of rounded metal.

Figure 2B:
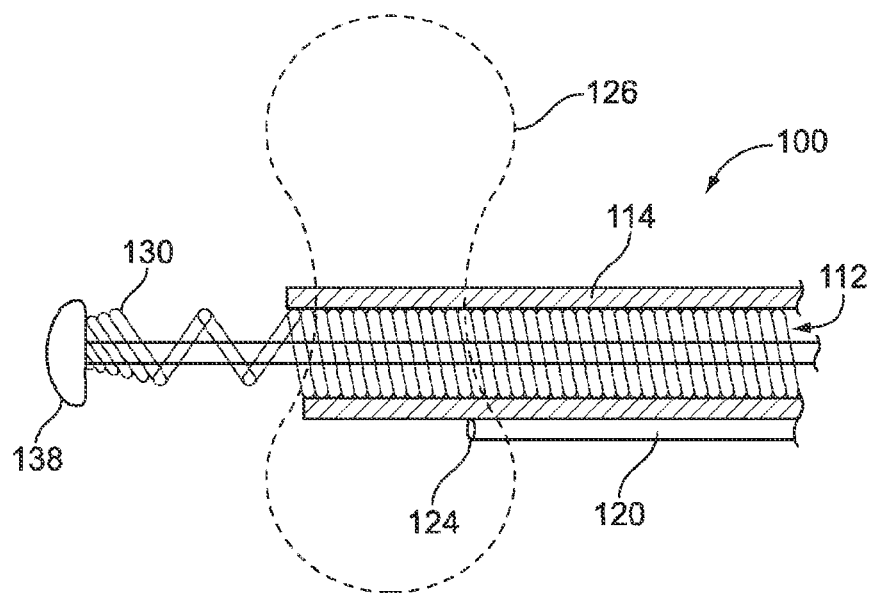
FIG. 2b presents a side elevational view of a portion of the catheter assembly between the distal and proximal ends in an alternative embodiment.

In another embodiment, the electrically conductive wire of the catheter assembly 100 is a helical electrically conductive wire 130 as shown in FIG. 2b. The wire 130 is a helical coil of wire that can also make contact with an electrical charge at the proximal portion 106 of the catheter assembly 100, in order to conduct an electrical charge down its entire length. As shown in FIG. 2b, the wire 130 will maintain a tightly wound nature from the central portion 104 through the proximal portion 106 of the catheter assembly 100. In the present embodiment, the helical electrically conductive wire 130 defines the central bore 112 through which a liquid may pass freely. At the distal portion 102 of the catheter assembly 100, the tight helix of the wire 130 will open up considerably for several revolutions of the helix, before the structure returns into a tightly wound nature at the. Attached to the wire 130 is a helical electrically conductive tip 132, which according to one embodiment, is a rounded tip made of a material capable of conducting an electrical current. According to one embodiment, the electrically conductive tip 132 is a piece of rounded metal. In this embodiment, the wire 130 is not covered by the sheath 114 at the distal portion 102 in order to allow the electrical charge to make contact with a target nerve.

Figure 3:
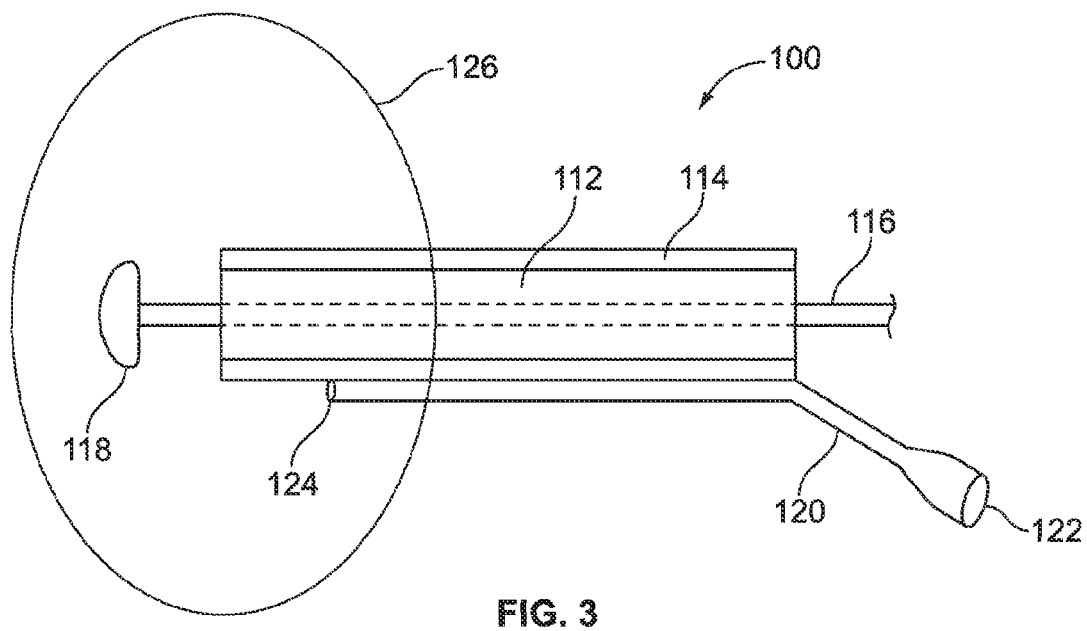
FIG. 3 presents a side elevational view of the catheter assembly in an expanded state.

Referring back to FIG. 1, the catheter assembly 100 further includes an inflatable balloon 126 that is located toward the distal end of the catheter assembly 100, as shown in FIG. 1 in a deflated state. The inflatable balloon 126 can be expanded with either a gaseous substance or a liquid substance, such as saline or a local anesthetic. A gaseous or liquid substance is delivered to the inflatable balloon 126 through a balloon channel 120. The balloon channel 120 terminates within the inflatable balloon 126, allowing for the gaseous or liquid substance to exit the balloon channel 120 through a balloon channel opening 124. The balloon channel 120 extends from the opening 124 along the length of the central portion 104 and the proximal portion 106 of the catheter assembly 100. At the proximal end of the channel 120 is a balloon channel injection opening 122, where the gaseous or liquid substance can be injected into the channel 120. Once the gaseous or liquid substance is injected into the channel 120, the gaseous or liquid substance is delivered to the balloon 126 through the opening 124, allowing for the balloon 126 to expand to an inflated state, as shown in FIG. 3. According to one embodiment, in its inflated state, the balloon 126 will have a diameter range of 0.1 to 3 cm.

Figure 4:
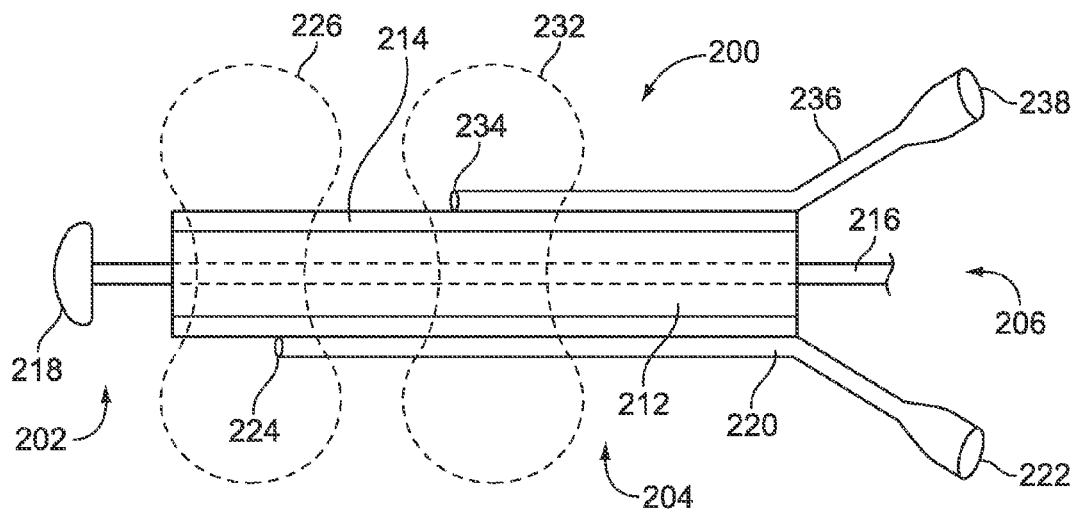
FIG. 4 presents a side elevational view of an alternative embodiment of the catheter assembly.

FIG. 4 side presents a side elevational view of an alternative embodiment of the present invention. A catheter assembly 200 is of a diameter which allows the assembly to be inserted through a typical needle assembly and into the body of a patient. The catheter assembly 200 includes three portions: a central portion 204, a proximal portion 206 and a distal portion 202. The catheter assembly 200 is placed in the body of the patient with the distal portion 202 entering the body first.

The catheter assembly 200 includes an electrically conductive wire 216 that spans the length of the catheter assembly 200. According to one embodiment, the wire 216 can be of helical nature with the same structure as described with reference to FIG. 2a. At the central portion 204 of the catheter assembly 200, a sheath 214, formed from a thermoplastic or some other similar material, covers the wire 216. The sheath 214 defines a central bore 212 through which a liquid may pass freely. According to another embodiment, where the wire 216 can be of helical nature, the electrically conductive wire 216 defines the central bore 212.

At the proximal portion 206 of the catheter assembly 200, the wire 216 is not covered by the sheath 214 and has a length that is shorter relative to central portion 204 of the catheter assembly 200. The wire 216 is left exposed so that an electrical charge can make contact with it, in order to conduct an electrical charge down its entire length.

The distal portion 202 of the catheter assembly 200 also has a length that is shorter relative to central portion 204 of the catheter assembly 200 and is not covered by the sheath 214. The wire 216 is left exposed at the distal portion 202 in order to allow the electrical charge to make contact with a target nerve. Attached to the wire 216 at the distal portion 202 is an electrically conductive tip 218, which is a piece of rounded metal.

The catheter assembly 200 further includes a first inflatable balloon 226 that is located toward the distal end of the catheter assembly 200, and a second inflatable balloon 232 that is located in the central portion 204 of the catheter assembly 200. Both first inflatable balloon 226 and the second inflatable balloon 232 are shown in FIG. 4 in a deflated state. The second balloon 232 is located a distance of in a range of zero (0) to ten (10) cm from the first balloon 226.

The first balloon 226 and the second balloon 232 can be expanded with either a gaseous substance or a liquid substance. A gaseous or liquid substance can be delivered to the first balloon 226 through a first balloon channel 220, which terminates within the first balloon 226, allowing for the gaseous or liquid substance to exit the first channel 220 through a first balloon channel opening 224. The first channel 220 extends from the first channel opening 224 along the length of the central portion 204 and the proximal portion 206 of the catheter assembly 200. At the proximal end of the first channel 220 is a first balloon channel injection opening 222 where the gaseous or liquid substance can be injected into the first channel 220.

Figure 5:
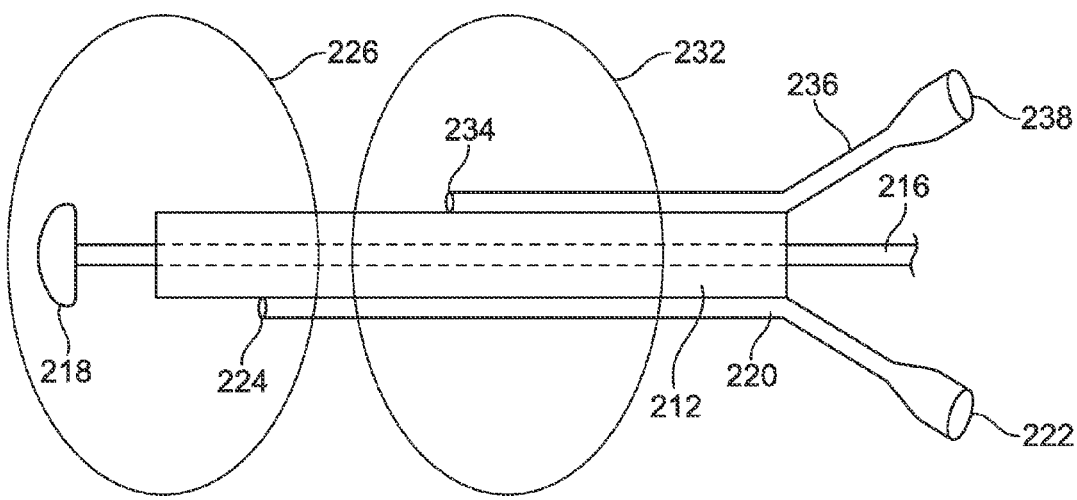
FIG. 5 presents a side elevational view of an alternative embodiment of the catheter assembly in an expanded state.

A gaseous or liquid substance can also delivered to the second inflatable balloon 232 through a second balloon channel 236, which terminates within the second balloon 232, allowing for the gaseous or liquid substance to exit the second channel 232 through a second balloon channel opening 234. The second channel 232 extends from the second opening 234 along the length of the central portion 204 and the proximal portion 206 of the catheter assembly 200. At the proximal end of the second channel 236 is a second balloon channel injection opening 238, where the gaseous or liquid substance can be injected into the second balloon channel 236. Once the gaseous or liquid substance is injected into the first balloon channel 220 or the second balloon channel 236, the gaseous or liquid substance is delivered to the first inflatable balloon 226 through the first balloon channel opening 224 and to the second inflatable balloon 232 through the second balloon channel opening 234. This allows for the first inflatable balloon 226 and the second inflatable balloon 232 to expand to an inflated state, as shown in FIG. 5. According to one embodiment, in its inflated state, the first inflatable balloon 226 and the second inflatable balloon 232 will each have a diameter range of 0.1 to 3 cm.

The above described apparatuses may be used in numerous different medical procedures. The following described medical procedure is one type that utilizes the features embodied in the above described apparatus pertaining to FIGS. 1-3. The method is drawn to the correct placement of the catheter assembly 100, which once correctly positioned, allows for the administration of a continuous nerve block such as a local anesthetic agent. In particular, the following described method is directed to the administration of an interscalene nerve block, which is used to describe only one example of the utilization of the above described apparatuses for the administration of a continuous nerve block. It should be noted that the above described apparatuses may be used for any continuous nerve block, of which the interscalene block is one example.

The patient is positioned in the dorsal recumbent position with the head slightly in extension and turned somewhat to the opposite side. An assistant applies light traction on the arm with the elbow flexed. The interscalene groove is palpated in this position by the following procedure: First, the posterior edge of the clavicular head of the sternocleidomastoid muscle is located; then the palpating fingers are placed postero-lateral to this muscle to identify the interscalene groove. The external jugular vein almost always lies directly superficial to the interscalene groove and provides a useful additional landmark. Needle entry should be anterior or posterior to the vein. Another constant finding is that the interscalene groove is approximately 3 cm lateral to the most prominent portion of the belly of the sternocleidomastoid muscle at the level of the cricoid cartilage.

A typical needle assembly is inserted into the interscalene groove at the level of the cricoid (C6 level) and the needle is directed perpendicular to the skin in all the planes. For the placement of the catheter assembly 100 for this continuous interscalene nerve block technique, the needle assembly enters the skin at a point approximately halfway between the mastoid and the clavicle, posterior to the posterior border of the clavicular head of the sternocleidomastoid muscle.

The point of needle entry is just caudal to the accessory nerve and just posterior to the anterior border of the posterior triangle of the neck. The tip of the typical needle assembly continues until it penetrates the fascia sheath of the brachial plexus using ultrasound technology. At this point, the needle assembly is in direct contact with the brachial plexus and, according to one embodiment, the central stylet of the needle assembly is removed and the catheter assembly 100 is fed through the needle to a point just past the tip of the needle. According to another embodiment, the catheter assembly 100 is placed over the length of the needle assembly to a point just past the tip of the needle. Such a placement of the electrically conductive tip 118 is far enough so that the electrically conductive wire 116 does not make contact with the needle, i.e. the needle tip is in contact with the catheter sheath 114 which will not conduct (disperse) electricity.

The electrically conductive wire 116 is then charged with an electrical charge by making contact with the electrically conductive wire 116 with a nerve stimulator as is known in the art. The output of the nerve stimulator can be typically in the range of approximately 0.5-1.0 mA as the muscle twitching will increase because all the current is now concentrated in the electrically conductive wire tip 118 of the catheter assembly 100. Once the catheter assembly is properly positioned, the inflatable balloon 126 is inflated in order to securely fix the catheter assembly 100, which is done with the assistance of ultrasound technology, as the inflatable balloon 126 is visible on an ultrasound. For example, air or saline is injected into the balloon channel injection opening 122, causing the air or saline to travel through the balloon channel 120 and to expand the inflatable balloon 126 to an inflated state (e.g. diameter of 5 mm).

Once the inflatable balloon 126 is fully expanded and the catheter assembly securely fixed, the typical needle assembly can then be removed and the local anesthetic may then be administered to effectuate a nerve block. When a dense motor and sensory block is required: (a) inject 20 mL of Ropivacaine 10 mg/mL (1%) as a bolus and then infuse with syringe driver a diluted concentration (5 mg/mL or 0.5%) at 10-20 mL/hour or (b) inject 20 mL of Bupivacaine 5 mg/mL (0.5%) as a bolus and then infuse a diluted concentration (2.5 mg/mL or 0.25%) at 10-20 mL/hour. When sensory block with minimal motor block is required: (a) inject 10-20 mL of Ropivacaine 2 mg/mL (0.2%) as a bolus and then infuse the same concentration at 1-10 mL/hour, continually adjusting the infusion rate to achieve the desired effect or (b) inject 10-20 mL of Bupivacaine 2.5 mg/mL (0.25%) as a bolus and the infuse the same concentration at 1-10 mL/hour, continually adjusting the infusion rate to achieve the desired effect. For Patient Controlled Interscalene Nerve Block, inject a bolus of 30 mL bupivacaine (0.4%) via an indwelling catheter into the brachial plexus sheath at the level of the interscalene groove followed by a background infusion of bupivacaine 0.15% at a rate of 5 mL/hour and a patient-controlled bolus of 4 mL for patients weighing>65 Kg and 3 mL for patients weighing<65 Kg.

In another embodiment of the present invention, a medical procedure utilizes the features embodied in the above-described apparatus pertaining to FIGS. 4-5. The method is drawn to the correct placement of the catheter assembly 200, which once correctly positioned, allows for the administration of a continuous nerve block such as a local anesthetic agent.

As described previously with respect to the medical procedure that utilizes the catheter assembly 100, the patient is positioned in the dorsal recumbent position with the head slightly in extension and turned somewhat to the opposite side. An assistant applies light traction on the arm with the elbow flexed.

The interscalene groove is palpated in this position and a typical needle assembly is inserted at the level of the cricoid (C6 level) and the needle is directed perpendicular to the skin in all the planes. For the placement of the catheter assembly 200 for this continuous interscalene nerve block technique, the needle assembly enters the skin at a point approximately halfway between the mastoid and the clavicle, posterior to the posterior border of the clavicular head of the sternocleidomastoid muscle.

The point of needle entry is just caudal to the accessory nerve and just posterior to the anterior border of the posterior triangle of the neck. The tip of the typical needle assembly continues until it penetrates the fascia sheath of the brachial plexus using ultrasound technology. At this point, the needle assembly is in direct contact with the brachial plexus and the central stylet of the needle assembly is removed and the catheter assembly 200 is fed through the needle to a point just past the tip of the needle. Such a placement of the electrically conductive tip 218 is far enough so that the electrically conductive wire 216 does not make contact with the needle, i.e. the needle tip is in contact with the catheter sheath 214 which will not conduct (disperse) electricity.

The wire 216 is then charged with an electrical charge by making contact with the wire 216 with a nerve stimulator. Once the catheter assembly is properly positioned, the first inflatable balloon 226 is inflated in order to securely fix the catheter assembly 200, which is done with the assistance of ultrasound technology, as the first balloon 226 is visible on an ultrasound. For example, air or saline is injected into the first balloon channel injection opening 222, causing the air or saline to travel through the first balloon channel 220 and to expand the first balloon 226 to an inflated state (e.g. diameter of 5 mm).

Once the first balloon 226 is fully expanded and the catheter assembly 200 securely fixed, the typical needle assembly can then be removed and the local anesthetic may then be administered to effectuate a nerve block. The first inflatable balloon 226 is then deflated and the second inflatable balloon 232 is inflated in order to maintain the catheter assembly 200 in place. The second balloon 232 is inflated in the same manner the first balloon 226 is inflated, where a liquid or gaseous substance is injected into the second balloon channel injection opening 238, causing the liquid or gas to travel through the second balloon channel 236, expanding the second inflatable balloon 232 to an inflated state (e.g. diameter of 5 mm). The first inflatable balloon 226 can also be inflated again in order to confirm that the catheter assembly is in the proper position via ultrasound.

The foregoing description of the specific embodiments so fully reveals the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A method for delivery of an anesthetic drug to a nerve of a patient, the method comprising: providing a catheter assembly capable of conveying an electrical impulse from a proximal end of the catheter assembly to a distal tip of the catheter assembly, the catheter assembly having an inflatable balloon at a distal end of the catheter assembly capable of being inflated with an injected substance; inserting the distal tip of the catheter assembly into the patient for placement of the distal tip near the nerve; applying the electrical impulse to the proximal end of the catheter assembly, which electrical impulse is conveyed to the distal tip of the catheter assembly; inflating the inflatable balloon at the distal end of the catheter assembly with the injected substance; wherein inflating the inflatable balloon at the distal end of the catheter assembly with the injected substance comprises: injecting the injected substance into a balloon channel injection opening of a balloon channel terminating within the inflatable balloon at the distal end of the catheter assembly; releasing the injected substance into the inflatable balloon at a balloon channel opening at a distal end of the balloon channel within the inflatable balloon; using ultrasound from a source external to the patient to view the inflatable balloon via the injected substance so as to manipulate the location of the catheter assembly proximate to the nerve; and administering the anesthetic drug through the catheter assembly to the nerve.

2. The method for delivery of an anesthetic drug to a nerve according to claim 1, wherein administering the anesthetic drug through the catheter assembly to the nerve comprises delivering the anesthetic drug to the proximate end of the catheter assembly, which anesthetic drug is conveyed to the distal tip of the catheter assembly.

\* \* \* \* \*